(12) United States Patent
Albaugh et al.

(10) Patent No.: US 6,720,339 B2
(45) Date of Patent: Apr. 13, 2004

(54) CERTAIN FUSED PYRROLECARBOXAMIDES; A NEW CLASS OF GABA BRAIN RECEPTOR LIGANDS

(75) Inventors: Pamela Albaugh, Carmel, IN (US); Gang Liu, Oak Park, CA (US); Alan Hutchison, Madison, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 10/090,935

(22) Filed: Mar. 5, 2002

(65) Prior Publication Data

US 2002/0198204 A1 Dec. 26, 2002

Related U.S. Application Data

(63) Continuation of application No. 09/088,522, filed on Jun. 1, 1998, now Pat. No. 6,353,109, which is a continuation of application No. 08/620,939, filed on Mar. 22, 1996, now abandoned.

(51) Int. Cl.[7] .................. A61K 31/403; A61K 31/4439
(52) U.S. Cl. ....................................... 514/339; 514/412
(58) Field of Search ...................... 546/278.1; 548/516; 514/339, 412

(56) References Cited

U.S. PATENT DOCUMENTS

| | | |
|---|---|---|
| 3,455,943 A | 7/1969 | Remers et al. |
| 4,075,343 A | 2/1978 | Kadin |
| 4,435,403 A | 3/1984 | Braestrup et al. |
| 4,442,295 A | 4/1984 | Michel et al. |
| 4,564,610 A | 1/1986 | Rahtz et al. |
| 4,596,808 A | 6/1986 | Braestrup et al. |
| 4,623,649 A | 11/1986 | Huth et al. |
| 4,719,210 A | 1/1988 | Seidelmann et al. |
| 4,736,043 A | 4/1988 | Michel et al. |
| 5,216,159 A | 6/1993 | Thurkauf et al. |
| 5,243,049 A | 9/1993 | Shaw et al. |
| 5,266,698 A | 11/1993 | Shaw et al. |
| 5,484,944 A | 1/1996 | Albaugh et al. |
| 5,608,079 A | 3/1997 | Albaugh et al. |
| 5,750,702 A | 5/1998 | Albaugh et al. |
| 5,925,770 A | 7/1999 | Albaugh et al. |
| 6,353,109 B1 * | 3/2002 | Albaugh et al. ......... 546/277.4 |

FOREIGN PATENT DOCUMENTS

| | | |
|---|---|---|
| WO | WO 93/17025 | 8/1994 |
| WO | WO 94/17095 | 8/1994 |
| WO | WO 95/11885 | 5/1995 |
| WO | WO 97/26243 | 7/1997 |

OTHER PUBLICATIONS

Carlock, et al., (1977) J. Org. Chem., 42:1883–1885.
H. Biere, et al. (1986) Liebigs Ann. Chem. 1749–1764.

* cited by examiner

Primary Examiner—Robert W. Ramsuer
(74) Attorney, Agent, or Firm—McDonnell Boehnen Hulbert & Berghoff

(57) ABSTRACT

Disclosed are compounds of the formula or the pharmaceutically acceptable non-toxic salts thereof wherein:

W represents substituted or unsubstituted aryl or heteroaryl;

T is hydrogen, halogen, hydroxyl, amino or alkyl;

X is hydrogen, hydroxy, or lower alkyl;

m is 0, 1, or 2;

n is 0, 1, or 2; and $R_3$ and $R_4$ represent substituted or unsubstituted organic residues.

These compounds are highly selective agonists, antagonists or inverse agonists for GABAa brain receptors or prodrugs of agonists, antagonists or inverse agonists for GABAa brain receptors These compounds are useful in the diagnosis and treatment of anxiety, sleep and seizure disorders, overdose with benzodiazepine drugs and for enhancement of memory.

47 Claims, No Drawings

CERTAIN FUSED PYRROLECARBOXAMIDES; A NEW CLASS OF GABA BRAIN RECEPTOR LIGANDS

This is a continuation of application Ser. No. 09/088,522, filed Jun. 1, 1998, now U.S. Pat. No. 6,353,109 which is a continuation of application Ser. No. 08/620,939, filed Mar. 22, 1996, now abandoned.

BACKGROUND OF THE INVENTION

1. Field of the Invention

This invention relates to certain fused pyrrolecarboxamides which selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness.

2. Description of the Related Art

γ-Aminobutyric acid (GABA) is regarded as one of the major inhibitory amino acid transmitters in the mammalian brain. Over 30 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic venal root reflex, a GABA-mediated event (Schmidt et al., 1967, Arch. Exp. Path. Pharmakol. 258: 69–82). All subsequent electrophysiological studies (reviewed in Tallman et al. 1980, Science 207: 274–81, Haefley et al., 1981, Handb. Exptl. Pharmacol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors; binding to these sites in vitro is rapid, reversible, stereospecific, and saturable. More importandy, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133: 249–60, Mohler & Okada, 1977, Science 12&: 854–51, Mohler & Okada, 1977, Br. J. Psychiatry 133: 261–68). The average therapeutic doses of these drugs in man also correlate with receptor potency (Tallman et al. 1980, Science 207: 274–281).

In 1978, it became clear that GABA and related analogs could interact at the low affinity (1 mM) GABA binding site to enhance the binding of benzodiazepines to the clonazepam-sensitive site (Tallman et al. 1978, Nature, 274: 383–85). This enhancement was caused by an increase in the affinity of the benzodiazepine binding site due to occupancy of the GABA site. The data were interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978, Nature, 274: 383–85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, triazolopyridazine interacted with benzodiazepine sites with a Hill coefficient of 1 (Squires et al., 1979, Pharma. Biochem. Behav. 10: 825–30, Klepner et al. 1979, Pharmacol. Biochem. Behav. 11: 457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther. 212: 337–46, Young et al., 1981 J. Phannacol Exp. ther 216: 425–430, Niehoff et al. 1982, J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 670–75).

A physical basis for the differences in drug specificity for the two apparent subtypes of benzodiazepine sites has been demonstrated by Sieghart & Karobath, 1980, Nature 286: 285–87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have molecular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "isoreceptors" or multiple allelic forms of the receptor (Tallman & Gallager 1985, Ann. Rev. Neurosci. 8, 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into $\alpha$, $\beta$, $\gamma$, $\delta$, $\epsilon$, and provide a molecular basis for the GABAa receptor heterogeneity and distinctive regional pharmacology (Shivvers et al., 1980; Levitan et al., 1989). The $\gamma$ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). The receptor binding assay is not totally predictive about the biological activity of such compounds; agonists, partial agonists, inverse agonists, and antagonists can inhibit binding. When the beta-carboline structure was determined, it was possible to synthesize a number of analogs and test these compounds behaviorally. It was immediately realized that the beta carbolines could antagonize the actions of diazepam behaviorally (Tenen & Hirsch, 1980, Nature 288: 609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit binding of benzodiazepines. The best studied of these compounds is an imidazodiazepine (Hunkeler et al., 1981, Nature 290: 514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunkeler et al., 1981, Nature 290: 514–16; Darragh et al., 1983, Eur. J. Clin. Pharmacol. 14: 569–70). When a radiolabeled form of this compound was studied (Mohler & Richards, 1981, Nature 294: 763–65), it was demonstrated that this compound would interact with the same number of sites as the benzodiazepines and beta-carbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous.

A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274: 383–85, Tallman et al., 1980, Science 207: 274–81), compounds with antagonist properties show little GABA shift (i.e., change in receptor affinity due to GABA) (Mohler & Richards 1981, Nature 294: 763–65), and the inverse agonists actually show a decrease in affinity due to GABA (Braestrup & Nielson 1981, Nature 294: 472–474). Thus, the GABA shift predicts generally the expected behavioral properties of the compounds.

Various compounds have been prepared as benzodiazepine agonists and antagonists. For Example, U.S. Pat. Nos. 3,455,943, 4,435,403, 4,596,808, 4,623,649, and 4,719,210, German Patent No. DE 3,246,932, and Liebigs Ann. Chem. 1986, 1749 teach assorted benzodiazepine agonists and antagonists and related anti-depressant and central nervous system active compounds.

U.S. Pat. No. 3,455,943 discloses compounds of the formula:

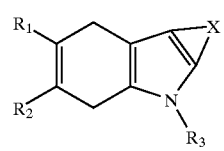

wherein $R_1$ is a member of the group consisting of hydrogen and lower alkoxy; $R_2$ is a member of the group consisting of hydrogen and lower alkoxy; $R_3$ is a member of the group consisting of hydrogen and lower alkyl; and X is a divalent radical selected from the group consisting of

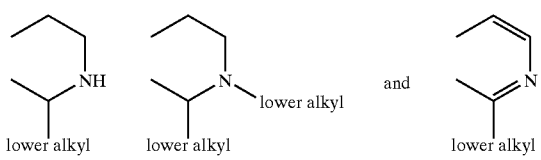

and the non-toxic acid addition salts thereof.

Other references, such as U.S. Pat. No. 4,435,403 and German patent DE 3,246,932 disclose compounds containing the following structural skeleton:

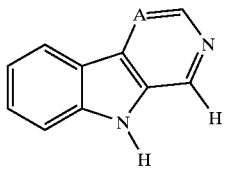

where A is carbon or nitrogen.

A variety of indole-3-carboxamides are described in the literature. For example, J. Org. Chem., 42: 1883–1885 (1977) discloses the following compounds.

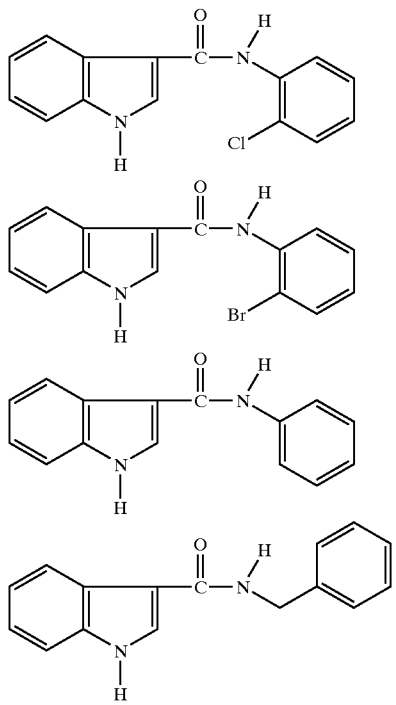

J. Heterocylic Chem., 14: 519–520 (1977) discloses a compound of the following formula:

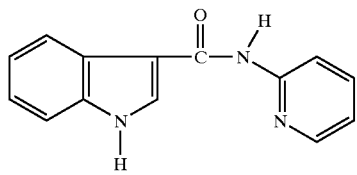

None of these indole-3-carboxamides includes an oxy substiuent at the 4-position of the indole ring.

U.S. Pat. No. 5,484,944, the disclosure of which is incorporated herein in its entirety, discloses compounds of the general formula:

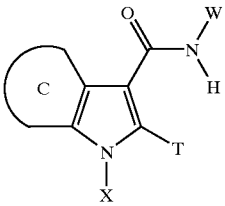

or the pharmacutically acceptable non-toxic salts thereof wherein:

T is halogen, hydrogen, hydroxyl, amino or straight or branched chain lower alkoxy having 1–6 carbon atoms;

X is hydrogen, hydroxyl or straight or branched chain lower alkyl having 1–6 carbon atoms;

W is phenyl, 2- or 3-thienyl, 2-, 3-, or 4-pyridyl or 6quinolinyl, each of which may be mono or disubstituted with halogen, cyano, hydroxy, straight or branched chain lower alkyl having 1–6 carbon atoms, amino, mono or dialkylamino where each alkyl is independently straight or branched chain lower alkyl having 1–6 carbon atoms, straight or branched chain lower alkoxy having 1–6 carbon atoms, or $NR_1COR_2$, $COR_2$, $CONR_1R_2$ or $CO_2R_2$ where $R_1$ and $R_2$ are the same or different and represent hydrogen or straight or branched chain lower alkyl having 1–6 carbon atoms; and

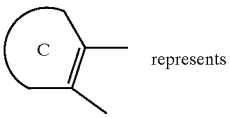 represents

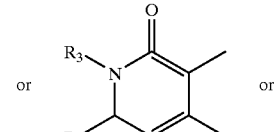

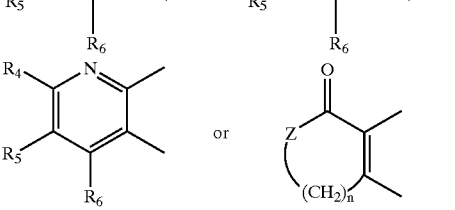

wherein:

Y represents nitrogen or $C-R_4$;

Z represents $N-R_7$ or a carbon atom substituted with $R_8$ and $R_9$, i.e., $C(R_8)(R_9)$;

n is 1, 2, 3, or 4;

$R_3$ is hydrogen, phenyl, 2-, 3-, or 4-pyridyl, straight or branched chain lower alkyl having 1–6 carbon atoms, or phenylalkyl or 2-, 3, or 4-pyridylalkyl where each alkyl is straight or branched chain lower alkyl having 1–6 carbon atoms;

$R_4$ is halogen or trifluoromethyl; or

—$OR_{10}$, —$COR_{10}$, —$CO_2R_{10}$, —$OCOR_{10}$, or —$R_{10}$, where $R_{10}$ is hydrogen, phenyl, 2,-3, or 4-pyridyl, straight or branched chain lower alkyl having 1–6 carbon atoms, or phenylalkyl or 2-, 3-, or 4-pyridylalkyl where each alkyl is straight or branched chain lower alkyl having 1–6 carbon atoms; or —$CONR_{11}R_{12}$ or —$(CH_2)_mNR_{11}R_{12}$, where m is 0, 1, or 2; $R_{11}$ represents hydrogen, straight or branched chain lower alkyl having 1–6 carbon atoms; and $R_{12}$ is hydrogen, phenyl, 2-, 3-, or 4-pyridyl, straight or branched chain lower alkyl having 1–6 carbon atoms, or phenylalkyl or 2-, 3-, or 4-pyridylalkyl where each alkyl is straight or branched chain lower alkyl having 1–6 carbon atoms; or $NR_{11}R_{12}$ forms a heterocyclic group which is morpholinyl, piperidinyl, pyrrolidinyl, or N-alkyl piperazinyl;

$R_5$ and $R_6$ are the same or different and represent hydrogen, halogen, straight or branched chain lower alkyl having 1–6 carbon atoms, or straight or branched chain lower alkoxy having 1–6 carbon atoms;

$R_7$ is hydrogen, phenyl, 2-, 3-, or 4-pyridyl, straight or branched chain lower alkyl having 1–6 carbon atoms, or phenylalkyl or 2-, 3-, or 4-pyridylalkyl where each alkyl is straight or branched chain lower alkyl having 1–6 carbon atoms;

$R_8$ is hydrogen or straight or branched chain lower alkyl having 1–6 carbon atoms; and $R_9$ is —$COR_{13}$, —$CO_2R_{13}$ or —$R_{13}$, where $R_{13}$ is hydrogen, phenyl, 2-, 3-, or 4-pyridyl, straight or branched chain lower alkyl having 1–6 carbon atoms, or phenylalkyl or 2-, 3-, or 4-pyridylalkyl where each alkyl is straight or branched chain lower alkyl having 1–6 carbon atoms; or —$CONR_{14}R_{15}$ or —$(CH_2)_kNR_{14}R_{15}$, where k is 0, 1, or 2; $R_{14}$ represents hydrogen, straight or branched chain lower alkyl having 1–6 carbon atoms; and $R_{15}$ is hydrogen, phenyl, 2-, 3-, or 4-pyridyl, straight or branched chain lower alkyl having 1–6 carbon atoms, or phenylalkyl or 2-, 3-, or 4-pyridylalkyl where each alkyl is straight or branched chain lower alkyl having 1–6 carbon atoms; or $NR_{14}R_{15}$ forms a heterocyclic group which is morpholinyl, piperidinyl, pyrrolidinyl, or N-alkyl piperazinyl.

International Application No. PCT/US94/12300, filed Oct. 26, 1994 and published May 4, 1995, the disclosure of which is incorporated herein in its entirety, also discloses pyrrole derivatives of the general formula described in U.S. Pat. No. 5,484,944, i.e.,

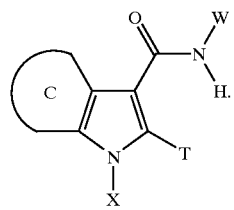

The substituents on this general formula are as defined in U.S. Pat. No. 5,484,944. In addition, U.S. application Ser. No. 08/473,509, filed Jun. 7, 1995, the disclosure of which is incorporated herein in its entirety, discloses compounds of the general formula set forth in U.S. Pat. No. 5,484,944.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in the diagnosis and treatment of anxiety, sleep and seizure disorders, overdose with benzodiazepine drugs and for enhancement of memory. Accordingly, a broad embodiment of the invention is directed to compounds of general Formula I:

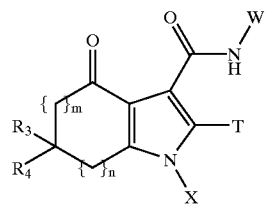

or the pharmaceutically acceptable non-toxic salts thereof wherein:

W is aryl or heteroaryl and

T is halogen, hydrogen, hydroxyl, amino or straight or branched chain lower alkoxy having 1–6 carbon atoms;

X is hydrogen, hydroxyl or straight or branched chain lower alkyl having 1–6 carbon atoms;

m is 0, 1, or 2;

n is 0, 1, or 2; and $R_3$ and $R_4$ are the same or different and are selected from hydrogen, straight or branched lower alkyl having 1–6 carbon atoms, $COR_5$ or $CO_2R_5$ where $R_5$ is straight or branched lower alkyl having 1–6 carbon atoms or cycloalkyl having 3–7 carbon atoms, $CONR_6R_7$ where $R_6$ and $R_7$ are selected independently from hydrogen, straight or branched chain lower alkyl having 1–6 carbon atoms, cycloalkyl having 3–7 carbon atoms, phenyl, 2-, 3-, or 4-pyridyl, or $NR_6R_7$ forms a heterocyclic group which is morpholinyl, piperidinyl, pyrrolidinyl, or N-alkyl piperazinyl; or $R_3$–$R_4$ together represent a cyclic moiety having 3–7 carbon atoms; and where each alkyl substituent in Formula I is optionally substituted with at least one group independently selected from hydroxy, mono- or dialkyl amino, phenyl or pyridyl.

These compounds are highly selective agonists, antagonists or inverse agonists for GABAa brain receptors or prodrugs of agonists, antagonists or inverse agonists for GABAa brain receptors. In other words, while the compounds of the invention all interact with GABAa brain receptors, they do not display identical physiologic activity. Thus, these compounds are useful in the diagnosis and treatment of anxiety, sleep and seizure disorders, overdose with benzodiazepine drugs and for enhancement of memory. For example, these compounds can be used to treat overdoses of benzodiazepine-type drugs as they would competitively bind to the benzodiazepine receptor.

DETAILED DESCRIPTION OF THE INVENTION

As used herein, the term "aryl" refers to aromatic carbocyclic groups having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be substituted with e.g., halogen, lower alkyl, lower alkylthio, trifluoromethyl, lower acyloxy, aryl, and heteroaryl.

A preferred aryl group is phenyl optionally substituted with up to five groups selected independently from halogen, cyano, hydroxy, straight or branched chain lower alkyl having 1–6 carbon atoms or cycloalkyl having 3–7 carbon atoms, amino, mono or dialkylamino where each alkyl is independently straight or branched chain lower alkyl having 1–6 carbon atoms or cycloalkyl having 3–7 carbon atoms, straight or branched chain lower alkoxy having 1–6 carbon atoms, cycloalkyl alkoxy having 3–7 carbon atoms, or $NR_1COR_2$, $COR_2$, $CONR_1R_2$ or $CO_2R_2$ where $R_1$ and $R_2$ are the same or different and represent hydrogen or straight or branched chain lower alkyl having 1–6 carbon atoms or cycloalkyl having 3–7 carbon atoms By heteroaryl is meant aromatic ring systems having at least one and up to four hetero atoms selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, napthyridinyl, isoxazolyl, phthalazinyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

The aryl and heteroaryl groups herein are systems characterized by $4n+2\pi$ electrons, where n is an integer.

In addition to those mentioned above, other examples of the aryl and heteroaryl groups encompassed within the invention are the following:

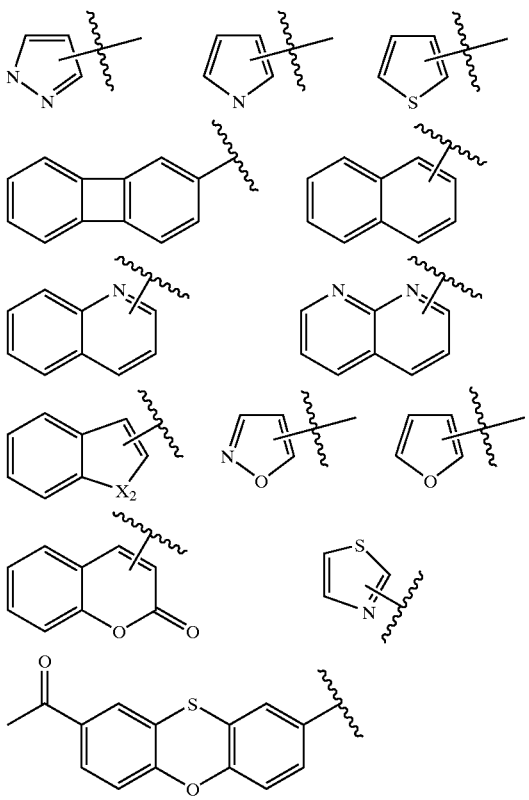

As noted above, each of these groups can optionally be mono- or polysubstituted with groups selected independently from, for example, halogen, lower alkyl, lower alkoxy, lower alkylthio, trifluoromethyl, lower acyloxy, aryl, heteroaryl, and hydroxy.

Still other examples of various aryl and heteroaryl groups are shown in Chart D of published International Application WO 93/17025.

By "alkyl" and "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Unless indicated otherwise, the alkyl group substituents herein are optionally substituted with at least one group independently selected from hydroxy, mono- or dialkyl amino, phenyl or pyridyl.

Where $R_3$ and $R_4$ are both alkyl, each alkyl is independently selected from lower alkyl.

By "alkoxy" and "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

As used herein "cycloalkyl alkoxy" refers to groups of the formula

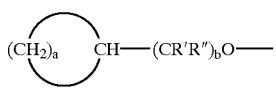

where a is an integer of from 2 to 6; R' and R" independently represent hydrogen or alkyl; and b is an integer of from 1 to 6.

By the term "halogen" in the present invention is meant fluorine, bromine, chlorine, and iodine.

By "N-alkylpiperazinyl" in the invention is meant radicals of the formula:

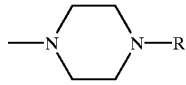

where R is alkyl as defined above.

By "monoalkylamino" as used herein is meant an amino substitutent substituted with one (1) alkyl group where the alkyl group is lower alkyl as defined above or cycloalkyl having from 3–7 carbon atoms.

By "dialkylamino" as used herein is meant an amino substitutent substituted with two (2) alkyl groups where the alkyl groups are independently lower alkyl groups as defined above or cycloalkyl groups having from 3–7 carbon atoms.

The novel compounds encompassed by the instant invention can be described by general Formula I set forth above and include the pharmaceutically acceptable non-toxic salts thereof.

In addition, the present invention encompasses compounds of Formula II.

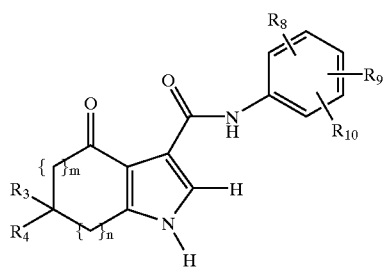

wherein $R_3$ and $R_4$ are the same or different and represent hydrogen, alkyl, $COR_5$ or $CO_2R_5$ where $R_5$ is alkyl or cycloalkyl having 3–7 carbon atoms, $CONR_6R_7$ where $R_6$ and $R_7$ are selected independently from hydrogen, alkyl, cycloalkyl having 3–7 carbon atoms, phenyl, 2-, 3-, or 4-pyridyl, or $NR_6R_7$ forms a heterocyclic group which is morpholinyl, piperidinyl, pyrrolidinyl, or N-alkyl piperazinyl; or $R_3$–$R_4$ together represent a cyclic moiety having 3–7 carbon atoms;

$R_8$ is hydrogen, halogen, hydroxyl, alkyl, alkoxy, cycloalkyl alkoxy having 3–7 carbon atoms, amino, mono- or dialkylamino; and $R_9$ is hydrogen, halogen, cyano, hydroxy, alkyl, alkoxy, cycloalkyl alkoxy having 3–7 carbon atoms, amino, mono- or dialkylamino, $NR_1COR_2$, $COR_2$, or $CO_2R_2$ where $R_1$ and $R_2$ are the same or different and represent hydrogen, alkyl, or cycloalkyl having 3–7 carbon atoms; and $R_{10}$ is hydrogen, halogen, hydroxyl, alkyl, alkoxy, amino, mono- or dialkylamino;

m is 0, 1, or 2; and n is 0, 1, or 2.

Preferred compounds of Formula II are those where the phenyl group is mono-, di-, or trisubstituted in the 2, 4, and/or 5 positions relative to the point of attachment of the phenyl ring to the amide nitrogen.

In addition, the present invention encompasses compounds of Formula III.

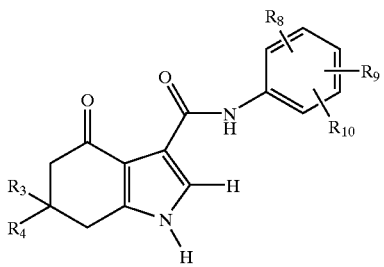

III wherein $R_3$ and $R_4$ are the same or different and represent hydrogen or alkyl;

$R_8$ is hydrogen, halogen, hydroxyl, alkyl, alkoxy, cycloalkyl alkoxy having 3–7 carbon atoms, amino, mono- or dialkylamino; and $R_9$ is hydrogen, halogen, cyano, hydroxy, alkyl, alkoxy, cycloalkyl alkoxy having 3–7 carbon atoms, amino, mono- or dialkylamino, $NR_1COR_2$, $COR_2$, or $CO_2R_2$ where $R_1$ and $R_2$ are the same or different and represent hydrogen, alkyl, or cycloalkyl having 3–7 carbon atoms; and $R_{10}$ is hydrogen, halogen, hydroxyl, alkyl, alkoxy, amino, mono- or dialkylamino.

Preferred compounds of Formula III are those where the phenyl group is mono-, di-, or trisubstituted in the 2, 4, and/or 5 positions relative to the point of attachment of the phenyl ring to the amide nitrogen. Particularly preferred compounds of Formula m are those where the phenyl group is trisubstituted in the 2, 4, and 5 positions relative to the point of attachment of the phenyl ring to the amide nitrogen, and $R_8$, $R_9$, and $R_{10}$ are independently selected from hydrogen, halogen, hydroxy, alkoxy, and alkyl, provided that not all of $R_8$, $R_9$, and $R_{10}$ are hydrogen.

In addition, the present invention encompasses compounds of Formula IV.

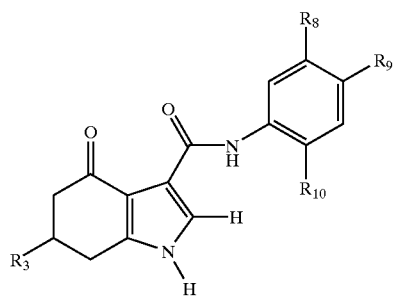

IV wherein $R_3$ represents alkyl;

$R_8$ is hydrogen, halogen, hydroxyl, alkyl, alkoxy, cycloalkyl alkoxy having 3–7 carbon atoms, amino, mono- or dialkylamino; and $R_9$ is hydrogen, halogen, cyano, hydroxy, alkyl, alkoxy, cycloalkyl alkoxy having 3–7 carbon atoms, amino, mono- or dialkylamino, $NR_1COR_2$, $COR_2$, or $CO_2R_2$ where $R_1$ and $R_2$ are the same or different and represent hydrogen, alkyl, or cycloalkyl having 3–7 carbon atoms; and $R_{10}$ is hydrogen, halogen, hydroxyl, alkyl, alkoxy, amino, mono- or dialkylamino.

Preferred compounds of Formula IV are those where $R_8$, $R_9$, and $R_{10}$ are independently selected from hydrogen, halogen, hydroxy, alkoxy, and alkyl, provided that not all of $R_8$, $R_9$, and $R_{10}$ are hydrogen.

In addition, the present invention encompasses compounds of Formula V.

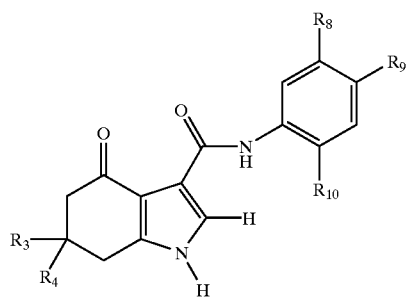

V wherein $R_3$ and $R_4$ independently represent alkyl;

$R_8$ is hydrogen, halogen, hydroxyl, alkyl, alkoxy, cycloalkyl alkoxy having 3–7 carbon atoms, amino, mon- or dialkylamino; and $R_9$ is hydrogen, halogen, cyano, hydroxy, alkyl, alkoxy, cycloalkyl alkoxy having 3–7 carbon atoms, amino, mono- or dialkylamino, $NR_1COR_2$, $COR_2$, or $CO_2R_2$ where $R_1$ and $R_2$ are the same or different and represent hydrogen, alkyl, or cycloalkyl having 3–7 carbon atoms; and $R_{10}$ is hydrogen, halogen, hydroxyl, alkyl, alkoxy, amino, mono- or dialkylamino.

Preferred compounds of Formula V are those where $R_8$, $R_9$, and $R_{10}$ are independently selected from hydrogen, halogen, hydroxy, alkoxy, and alkyl, provided that not all of $R_8$, $R_9$, and $R_{10}$ are hydrogen. Particularly preferred compounds of Formula V are those where $R_3$ and $R_4$ are both methyl, and $R_8$, $R_9$, and $RR_{10}$ are independently selected from hydrogen, halogen, hydroxy, alkoxy, and alkyl, provided that not all of $R_8$, $R_9$, and $R_{10}$ are hydrogen.

In addition, the present invention encompasses compounds of Formula VI

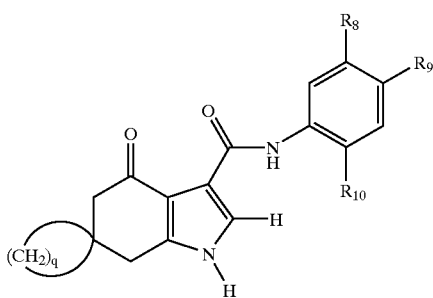

VI wherein
  q is an integer of from 2–6;
  $R_8$ is hydrogen, halogen, hydroxyl, alkyl, alkoxy, cycloalkyl alkoxy having 3–7 carbon atoms, amino, mono- or dialkylamino; and
  $R_9$ is hydrogen, halogen, cyano, hydroxy, alkyl, alkoxy, cycloalkyl alkoxy having 3–7 carbon atoms, amino, mono- or dialkylamino, $NR_1COR_2$, $COR_2$, or $CO_2R_2$ where $R_1$ and $R_2$ are the same or different and represent hydrogen, alkyl, or cycloalkyl having 3–7 carbon atoms; and
  $R_{10}$ is hydrogen, halogen, hydroxyl, alkyl, alkoxy, amino, mono- or dialkylamino;
  m is 0, 1, or 2; and
  n is 0, 1, or 2.

Preferred compounds of Formula VI are those where $R_8$, $R_9$, and $R_{10}$ are independently selected from hydrogen, halogen, hydroxy, alkoxy, and alkyl, provided that not all of $R_8$, $R_9$, and $R_{10}$ are hydrogen.

In addition, the present invention encompasses compounds of Formula VII:

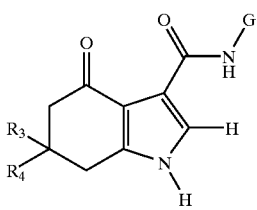

VII where
  G represents aryl or heteroaryl such as, for example, thienyl, thiazolyl, pyridyl, napthyridinyl, quinolinyl, or phenyl, each of which is optionally mono-, di- or trisubstituted with halogen, alkyl, alkoxy, or hydroxy; and
  $R_3$ and $R_4$ are the same or different and represent hydrogen or alkyl, provided that not both $R_3$ and $R_4$ are hydrogen.

Preferred compounds of Formula VII are those where $R_3$ and $R_4$ are $C_{1-3}$ alkyl, and more preferably methyl. Other preferred compounds of Formula VII are those where $R_3$ is hydrogen and $R_4$ is $C_{1-3}$ alkyl, and more preferably $R_4$ is methyl.

Preferred compounds of Formula VII include a G group selected from the following:

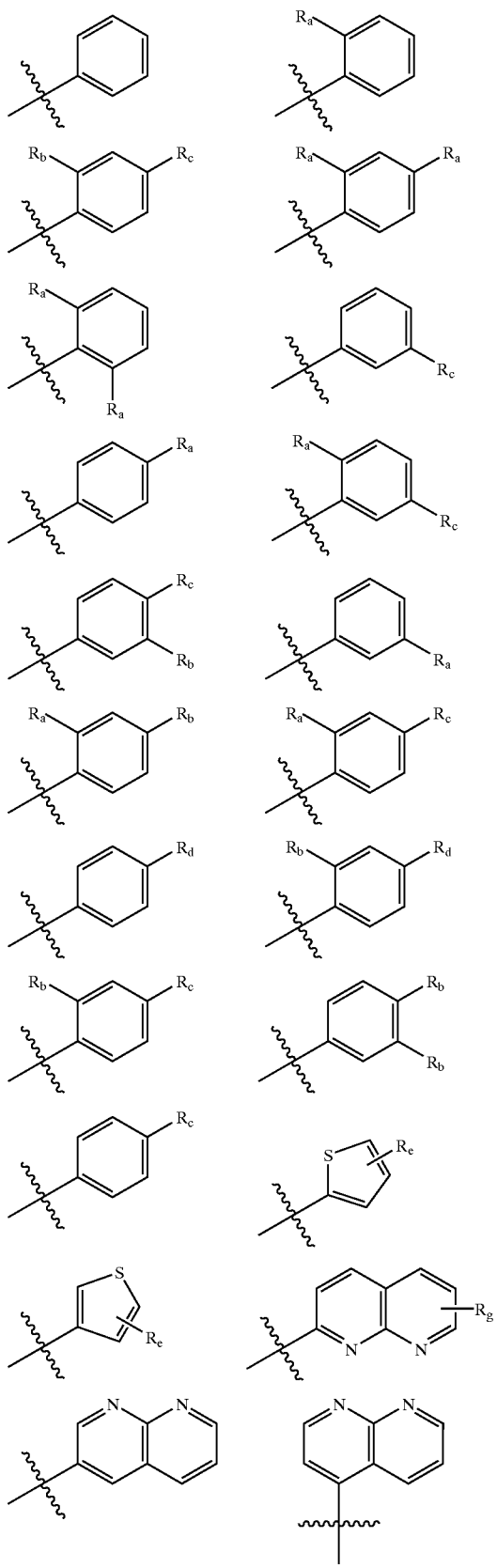

In the above G groups, the following definitions apply:

$R_a$ is halogen;

$R_b$ is hydroxy;

$R_c$ represents alkoxyl, $R_d$ represents alkyl;

$R_e$ represents hydrogen or $R_d$;

$R_f$ represents hydrogen, or $R_c$; and $R_g$ represents hydrogen, $R_a$ or $R_c$.

In those formulas where more than one of the same substituent appears, those substituents are the same or different Particularly preferred $R_a$ groups in G are fluorine. Particularly preferred $R_c$ groups in G are methoxy and ethoxy. Particularly preferred $R_d$ groups in G are methyl and ethyl.

Representative compounds of the invention are shown below in Table 1.

TABLE 1-continued

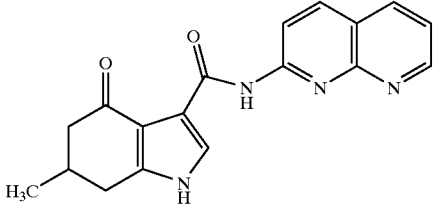

Compound 9

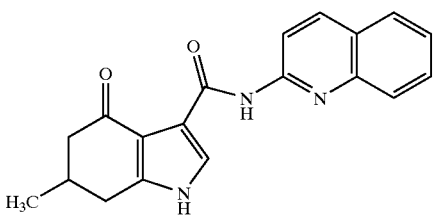

Compound 10

The following numbering system is used to identify positions on the pyrrole ring portion of the compounds of the invention:

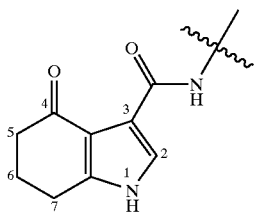

Representative compounds of the present invention, which are encompassed by Formula I, include, but are not limited to the compounds in Table I and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic phamaceutically acceptable addition salts.

The present invention also encompasses the prodrugs, preferably acylated prodrugs, of the compounds of Formula I. Those skilled in the art will recognize various synthetic methodologies which may be employed to prepare non-toxic pharmaceutically acceptable addition salts and acylated prodrugs of the compounds encompassed by Formula I.

The pharmaceutical utility of compounds of this invention are indicated by the following assay for GABAa receptor binding activity.

Assays are carried out as described in Thomas and Tallman (J. Bio. Chem. 156: 9838–9842, J. Neurosci. 3: 433–440, 1983). Rat cortical tissue is dissected and homogenized in 25 volumes (w/v) of 0.05 M Tris HCl buffer (pH 7.4 at 4° C.). The tissue homogenate is centrifuged in cold (4° C.) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (orginal wt/vol) of buffer and the procedure is carried out twice. The pellet is finally resuspended in 50 volumes (w/vol of 0.05 M Tris HCl buffer (pH 7.4 at 40° C.).

Incubations contain 100 ml of tissue homogenate, 100 ml of radioligand 0.5 nM ($^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to Ki's; results for compounds of this invention are listed in Table 2.

TABLE 2

| Compound Number | $K_i$ (nM) |
|---|---|
| 1 | 21 |
| 2 | 12 |
| 3 | 13 |
| 4 | 1 |
| 5 | 0.5 |
| 6 | 1 |
| 7 | 10 |
| 8 | 80 |
| 9 | 4 |
| 10 | 12 |

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostrate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectable.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Scheme I.

Scheme I

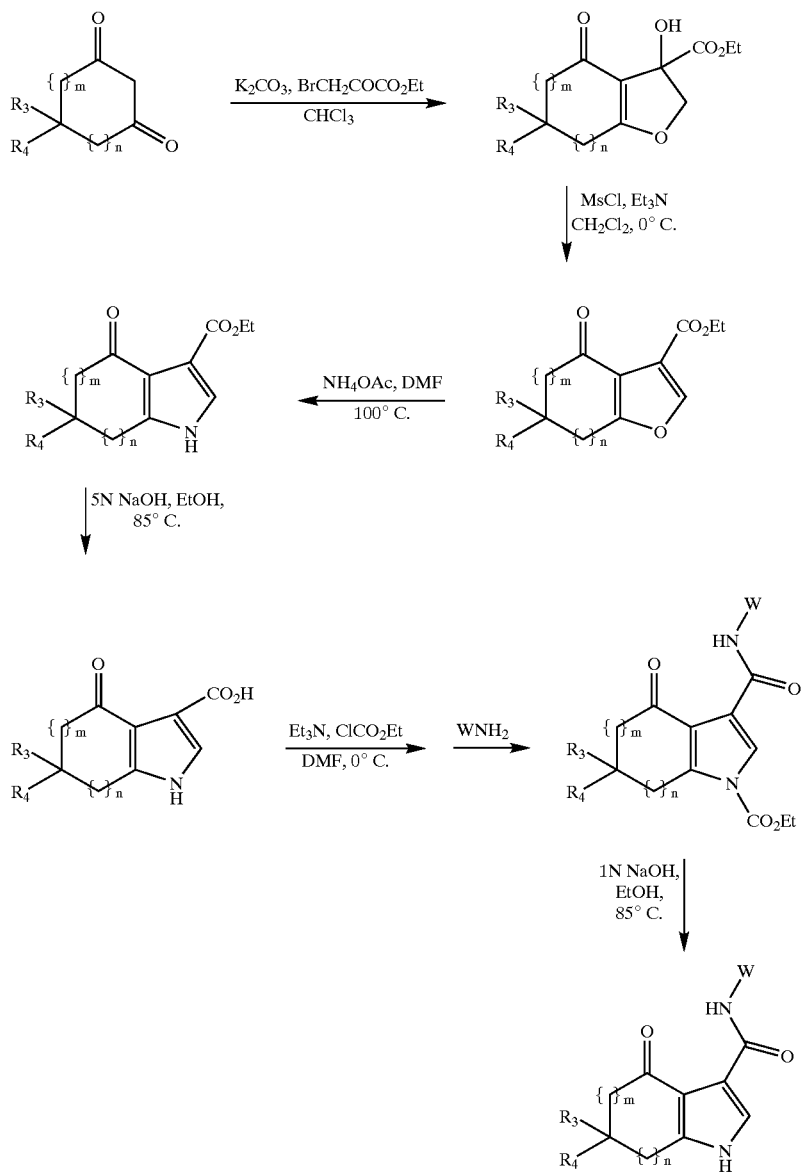

where W, m, n, $R_3$, and $R_4$ are defined as above.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The disclosures in this application of all articles and references, including patents, are incorporated herein by reference in their entirety.

The invention is illustrated further by the following examples which are not to be construed as limiting the invention in scope or spirit to the specific procedures described in them.

EXAMPLE 1

Preparation of Strating Materials and Intermediates

The starting materials and various intermediates may be obtained from commercial sources, prepared from commercially available organic compounds, or prepared using well known synthetic methods.

Representative examples of methods for preparing intermediates of the invention are set forth below.

1. Ethyl 3-hydroxy 4-oxo-6-methyl-2,3,4,5,6,7-hexahydrobenzofuran-3-carboxylate

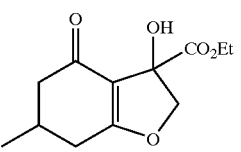

To a stirred mixture of 5-methyl-1,3-cyclohexanedione (10.25 g, 81 mmol) and potassium carbonate (22.46 g, 162 mmol) in dichloromethane (200 mL) at 0° C. was added a solution of ethyl bromopyruvate (10.7 mL, 85 mmol) in dichloromethane (50 mL). The reaction was allowed to reach ambient temperature, stirred for 18 hours, then poured into saturated aqueous ammonium chloride. After adjusting to neutral pH with aqueous hydrochloric acid, the mixture was extracted 2x with dichloromethane, the combined organic layers were dried over sodium sulfate, filtered, and concentrated in vacuo to give ethyl 3-hydroxy 4-oxo-6methyl-2,3,4,5,6,7-hexahydrobenzofuran-3-carboxylate (18.48 g).

2. Ethyl 4-oxo-6-methyl-4,5,6,7-tetrahydrobenzofuran-3-carboxylate

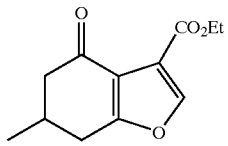

A solution of methanesulfonyl chloride (6.1 ml, 78.5 mmol) in dichloromethane (50 mL) was added to a stirring solution of ethyl 3-hydroxy 4-oxo-6-methyl-2,3,4,5,6,7-hexahydrobenzofuran-3-carboxylic acid (18.48 g, 76 mmol) and triethylamine (21.4 mL, 154 mmol) in dichloromethane (150 mL) at 0° C. The mixture was allowed to reach ambient temperature, stirred for 2 hours, then poured into aqueous 1N sodium hydroxide and extracted with ethyl acetate. The organic layer was washed with brine, dried over magnesium sulfate, filtered, and concentrated in vacuo to give ethyl 4-oxo-6-methyl-4,5,6,7-tetrahydrobenzofuran-3-carboxylate (16.86 g).

3. 4-Oxo-6-methyl-4,5,6,7-tetrahydro-1H-indole-3-carboxylic acid

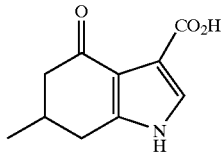

A stirred mixture of ethyl 4-oxo-6-methyl-4,5,6,7-tetrahydrobenzofuran-3-carboxylate (15.7 g, 71 mmol) and ammonium acetate (9.54 g, 124 mmol) in N,N,-dimethylformamide (75 mL) was heated at 100° C. for 2 hour The reaction mixture was concentrated in vacuo, ice water was added, and the precipitate collected, rinsed with water then diethyl ether and dried to give ethyl 4-oxo-6-methyl-4,5,6,7-tetrahydro-1H-indole-3-carboxylate (5.94 g). To this ester was added aqueous 5N sodium hydroxide (50 mL) and ethyl alcohol (10 mL) and the mixture heated at reflux for 40 minutes. The reaction mixture was cooled in an ice water bath, acidified with aqueous hydrochloric acid, and the precipitate collected, rinsed with water then diethyl ether and dried to give 4-oxo-6-methyl-4,5,6,7-tetrahydro-1H-indole-3-carboxylic acid (5.2 g). m.p. 210–211° C.

4. 4-Oxo-6,6dimethyl-4,5,6,7-tetrohydro-1H-indole-3carboxylic acid (m.p. 231–232° C.) was prepared essentially according to the procedures described in Parts 1–3 of this examples.

EXAMPLE 2

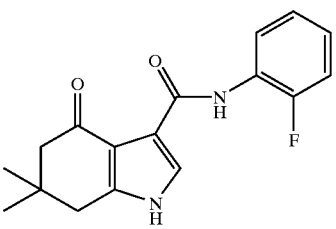

To a stirred solution of 4-oxo-6,6-dimethyl-4,5,6,7-tetrahydro-1H-indole-3-carboxylic acid (155 mg, 0.75 mmol) and triethylamine (209 µL, 1.5 mmol) in dimethylformamide (4 mL) at 0° C. was added ethyl chloroformate (143 µL, 1.5 mmol). After stirring an additional 45 minutes, 2-fluoroaniline (145 µL, 1.5 mmol) was added. The reaction mixture was stirred for 30 minutes, then poured into aqueous 3.6N hydrochloric acid and extracted 2x with ethyl acetate. The combined organic layers were washed with water, dried over magnesium sulfate, filtered, and concentrated in vacuo. To the residue was added aqueous 5N sodium hydroxide (5 mL) and ethyl alcohol (1 mL), and the mixture was heated at reflux for 30 minutes. After cooling in an ice water bath, the reaction mixture was acidified with hydrochloric acid, the precipitate was collected, rinsed with water, and dried to give 55 mg of N-(2-fluorophenyl)-4-oxo-6,6-dimethyl-4,5,6,7-tetrahydro-1H-indole-3 oxamide (Compound 2).

EXAMPLE 3

The following compounds are prepared essentially according to the procedures described in Examples 1 and 2.
(a) N-Phenyl-4-oxo-6,6-dimethyl-4,5,6,7-tetrahydro-1H-indole-3-carboxamide (Compound 1).
(b) N-(3-Fluorophenyl)-4-oxo-6,6-dimethyl-4,5,6,7-tetrahydro-1H-indole-3-carboxamide; mp 259–261° C.
(c) N-(4-Fluorophenyl)-4-oxo-6,6-dimethyl-4,5,6,7-tetrahydro-1H-indole-3-carboxamide; mp 268–270° C.
(d) N-(2,4-Difluorophenyl)-4-oxo-6,6-dimethyl-4,5,6,7-tetrahydro-1H-indole-3-carboxamide.
(e) N-(2,6-Difluorophenyl)-4-oxo-6,6-dimethyl-4,5,6,7-tetrahydro-1H-indole-3-carboxamide.
(f) N-(3-Methoxyphenyl)-4-oxo-6,6-dimethyl-4,5,6,7-tetrahydro-1H-indole-3-carboxamide.
(g) N-(2-Hydroxy-4-methoxyphenyl)-4-oxo-6,6-dimethyl-4,5,6,7-tetrahydro-1H-indole-3-carboxamide; mp 190–192° C.
(h) N-(3-Hydroxy-4-methoxyphenyl)-4-oxo-6,6-dimethyl-4,5,6,7-tetrahydro-1H-indole-3-carboxamide; mp 282–284° C.
(i) N-(2-Fluoro-4-methoxyphenyl)-4-oxo-6,6-dimethyl-4,5,6,7-tetrahydro-1H-indole-3-carboxamide; mp 213–215° C.
(j) N-(2-Fluoro-4-ethoxyphenyl)-4-oxo-6,6-dimethyl-4,5,6,7-tetrahydro-1H-indole-3-carboxamide.
(k) N-(2-Fluoro-5-methoxyphenyl)-4-oxo-6,6-dimethyl-4,5,6,7-tetrahydro-1H-indole-3-carboxamide.
(l) N-(2-Fluoro-4-hydroxyphenyl)-4-oxo-6,6-dimethyl-4,5,6,7-tetrahydro-1H-indole-3-carboxamide; mp 225–227° C.
(m) N-(4-Methoxyphenyl)-4-oxo-6,6-dimethyl-4,5,6,7-tetrahydro-1H-indole-3-carboxamide (Compound 3).
(n) N-(4-Ethoxyphenyl)4-oxo-6,6-dimethyl-4,5,6,7-tetrahydro-1H-indole-3-carboxamide.
(o) N-(4-Methylphenyl)-4-oxo-6,6-dimethyl-4,5,6,7-tetrahydro-1H-indole-3-carboxamide.

(p) N-(2-Hydroxy-4-methylphenyl)-4-oxo-6,6-dimethy-4,5,6,7-tetrahydro-1H-indole-3carboxamide; mp 201–203° C.

(q) N-Phenyl-4-oxo-6-methyl-4,5,6,7-tetraydro-1H-indole-3-carboxamide (Compound 4); mp 278–279° C.

(r) N-(2-Fluorophenyl)-4-oxo-6-methyl-4,5,6,7-tetrahydro-1H-indole-3-carboxamide (Compound 5); mp 264–265° C.

(s) N-(3-Fluorophenyl)-4-oxo-6-methyl-4,5,6,7-tetrahydro-1H-indole-3-carboxamide; mp 302–303° C.

(t) N-(4-Fluorophenyl)-4-oxo-6-methyl-4,5,6,7-tetrahydro-1H-indole-3-carboxamide; mp 262–264° C.

(u) N-(3-Methoxyphenyl)-4-oxo-6-methyl-4,5,6,7-tetrahydro-1H-indole-3-carboxamide; mp 234–235° C.

(v) N-(4-Hydroxyphenyl)-4oxo-6-methyl-4,5,6,7-tetrahydro-1H-indole-3-carboxamide; mp 320° C.

(w) N-(2-Fluoro-4-hydoxyphenyl)-4-oxo-6-methyl-4,5,6,7-tetrahydro-1H-indole-3-carboxamide; mp 330° C.

(x) N-(2-Hydroxy-4-methoxyphenyl)-4-oxo-6methyl-4,5,6,7-tetrahydro-1H-indole-3-carboxamide; mp 236–238° C.

(y) N-(4-Methoxyphenyl)-4-oxo-6-methyl-4,5,6,7-tetrahydro-1H-indole-3-carboxamide; mp 260–261° C.

(z) N-(2-Fluoro-4-methoxyphenyl)-4-oxo-6-methyl-4,5,6,7-tetrahydro-1H-indole-3-carboxamide (Compound 6); mp 217–219° C.

(aa) N-(4-Ethoxyphenyl)-4-oxo-methyl-4,5,6,7-tetrahydro-1H-indole-3-carboxamide; mp 269° C.

(bb) N-(2-Fluoro-4-ethoxyphenyl)-4-oxo-6-methyl-4,5,6,7-tetrahydro-1H-indole-3-carboxamide; mp 224–225° C.

(cc) N-(3,4-Dihydroxyphenyl)-4-oxo-6-methyl-4,5,6,7-tetrahydro-1H-indole-3-carboxamide; mp 267–269° C.

(dd) N-(2-Hydroxy-4-methylphenyl)-4-oxo-6-methyl-4,5,6,7-tetrahydro-1H-indole-3-carboxamide; mp 258–260° C.

(ee) N-(3-Thienyl)-4-oxo-6,6-dimethyl-4,5,6,7-tetrahydro-1H-indole-3-caboxamide (Compound 7).

(ff) N-(2-Thiazoly)-4-oxo-6,6-dimethyl-4,5,6,7-tetrahydro-1H-indole-3-carboxamide.

(gg) N-(5-Methyl-2-thiazolyl)-4-oxo-6,6-dimethyl-4,5,6,7-tetrahydro-1H-indole-3-carboxamide.

(hh) N-(3-Pyridyl)-4-oxo-6,6-dimethyl-4,5,6,7-tetrahydro-1H-indole-3-carboxamide; mp 237–239° C.

(ii) N-(4-Methoxy-3-pyridyl)-4-oxo-6,6-dimethyl-4,5,6,7-tetrahydro-1H-indole-3-carboxamide; mp 217–218C.

(jj) N-(2-Chloro-1,8-napthyridin-7-yl)-4-oxo-6,6-dimethyl-4,5,6,7-tetrahydro-1H-indole-3-carboxamide; mp 278–280° C.

(kk) N-(1,8-Napthyridin-2yl)-4-oxo-6,6-dimethyl-4,5,6,7-tetrahydro-1H-indole-3-carboxamide (compound 8); mp 389–390° C.

(ll) N-(3-Pyridyl)-4-oxo-6-methyl-4,5,6,7-tetrahydro-1H-indole-3-carboxamide; mp 225–227° C.

(mm) N-(4-Pyridyl)-4-oxo-6-methyl-4,5,6,7-tetrahydro-1H-indole-3-carboxamide; mp 280–290° C.

(nn) N-(1,8-Napthyridin-2-yl)-4-oxo-6-methyl-4,5,6,7-tetahydro-1H-indole-3-carboxamide (Compound 9).

(oo) N-(6-Methyl-1,8-napthridin-2-yl)-4-oxo-6-methyl-4,5,6,7-tetrahydro-1H-indole-3-carboxamide; mp 338–340° C.(d).

(pp) N-(2-Quinolinyl)-4-oxo-6-methyl-4,5,6,7-tetrahydro-1H-indole-3-carboxamide (Compound 10); mp 273–275° C.

(qq) N-(4-Pyridyl)-4-oxo-6,6-dimethyl-4,5,6,7-tetrahydro-1H-indole-3-carboxmide.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A pharmaceutical composition comprising a compound of the formula:

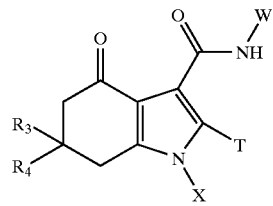

or a pharmaceutically acceptable non-toxic salt thereof wherein:

w is aryl or 2-, 3-, or 4-pyridyl, each or which is optionally substituted with up to Live groups selected independently from halogen, cyano, hydroxy, alkyl or cyclcalkyl having 3–7 carbon atoms, amino or mono- or dialkylamino where each alkyl is independently lower alkyl or cycloalkyl having 3–7 carbon atoms, alkoxy or cycloalkyl alkoxy having 3–7 carbon atoms, or $NR_1CCR_2$, $COR_2$, $CONR_1R_2$ or $CO_2R_2$ where $R_1$ and $R_2$ are the same or different and represent hydrogen or alkyl or cycloalkyl having 3–7 carbon atoms; and T is hydrogen;

X is hydrogen, hydroxyl or alkyl;

$R_3$ and $R_4$ are the same or different and represent hydrogen or alkyl, provided that not both $R_3$ and $R_4$ are hydrogen, together with at least one pharmaceutically acceptable carrier.

2. A pharmaceutical composition comprising a compound of the formula:

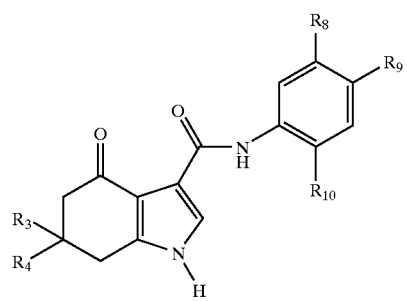

wherein $R_3$ and $R_4$ are the same or different and represent hydrogen or alkyl, provided that not both $R_3$ and $R_4$ are hydrogen;

$R_8$ is hydrogen, halogen, hydroxyl, alkyl, alkoxy, cycloalkyl alkoxy having 3–7 carbon atoms, amino, mono- or dialkylamino; and $R_9$ is hydrogen, halogen, cyano, hydroxy, alkyl, alkoxy, cycloalkyl alkoxy having 3–7 carbon atoms, amino, mono- or dialkylamino, $NR_1COR_2$, $COR_2$, or $CO_2R_2$ where $R_1$ and $R_2$ are the same or different and represent hydrogen, alkyl, ox cycloalkyl having 3–7 carbon atoms; and R<sub>10</sub> is hydrogen, halogen, hydroxyl, alkyl, alkoxy, amino, mono- or dialkylamino,
together with at least one pharmaceutically acceptable carrier.

3. A pharmaceutical composition comprising a compound of the formula:

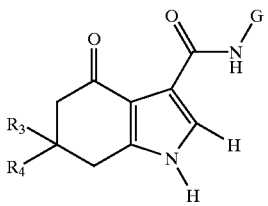

where
G represents pyridyl or phenyl, each of which is optionally mono-, di- or trisubstituted with halogen, alkyl, alkoxy, or hydroxy; and
$R_3$ and $R_4$ are the same or different and represent hydrogen or alkyl, provided that not both $R_3$ and $R_4$ are hydrogen, together with at least one pharmaceutically acceptable carrier.

4. A pharmaceutical composition according to claim 3, wherein $R_3$ and $R_4$ are $C_{1-3}$ alkyl.

5. A pharmaceutical composition according to claim 3, wherein $R_3$ and $R_4$ are methyl.

6. A pharmaceutical composition according to claim 3, wherein $R_3$ is methyl and $R_3$ is hydrogen.

7. A pharmaceutical composition according to claim 1, comprising a compound which is W-Phenyl-4-oxo-6.6-dimethyl-4,5,6,7-tetrahydro-1H-indole-3-carboxamide.

8. A pharmaceutical composition according to claim 1, comprising a compound which is N-(2-Fluorophenyl)-4-oxo-6,6-dimethyl-4,5,6,7-tetrahydro-1H-indole-3-carboxamide.

9. A pharmaceutical composition according to claim 1, comprising a compound which is N-(3-Fluorophenyl)-4-oxo-6,6-dimethyl-4,5,6,7-tetrahydro-1H-indole-3-carboxamide.

10. A pharmaceutical composition according to claim 1, comprising a compound which is N-(4-Fluorophenyl)-4-oxo-6,6-dimethyl-4,5,6,7-tetrahydro-1H-indole-3-carboxamide.

11. A pharmaceutical composition according to claim 1, comprising a compound which is N-(2,4-Difluorophenyl)-4-oxo-6,6-dimethyl -4,5,6,7-tetrahydro-1H-indole-3-carboxamide.

12. A pharmaceutical composition according to claim i, comprising a compound which is N-(2,6-Difluorophenyl)-4-oxo-6,6-dimethyl-4,5,6,7-tetrahydro-1H-indole-3-carboxamide.

13. A pharmaceutical composition according to claim 1, comprising a compound which is N-(3-Methoxyphenyl)-4-oxo-6,6-dimethyl-4,5,6,7-tetrahydro-1H-indole-3-carboxamide.

14. A pharmaceutical composition according to claim 1, comprising a compound which is N-(2-1H-indole-3-carboxamide.

15. A pharmaceutical composition according to claim 1, comprising a compound which is N-(3-Hydroxy-4-methoxyphenyl)-4-oxo-6,6-dimethyl-4,5,6,7-tetrahydro-1H-indole-3-carboxamide.

16. A pharmaceutical composition according to claim 1, comprising a compound which is N-(2-Fluoro-4-methoxyphenyl)-4-oxo-6,6-dimethyl-4,5,6,7-tetrahydro-1H-indole-3-carboxamide.

17. A pharmaceutical composition according to claim 1, comprising a compound which is N-(2-Fluoro-4-ethoxyphenyl)-4-oxo-6,6-dimethyl-4,5,6,7-tetrabydro-1H-indole-3-carboxamide.

18. A pharmaceutical composition according to claim 1, comprising a compound which is N-(2-Fluoro-5-methoxyphenyl)-4-oxo-6,6-dimethyl-4,5,6,7-tetrahydro-1H-indole-3-carboxamide.

19. A pharmaceutical composition according to claim 1, comprising a compound which is N-(2-Fluoro-4-hydroxyphenyl)-4-oxo-6,6-dimethyl-4,5,6,7-tetrahydro-1H-indole-3-carboxamide.

20. A pharmaceutical composition according to claim 1, comprising a compound which is N-(4-Methoxyphenyl)-4-oxo-6,6-dimethyl-4,5,6,7-tetrahydro-1H-indole-3-carboxamide.

21. A pharmaceutical composition according to claim 1, comprising a compound which is N-(4-Methylphenyl)-4-oxo-6,6-dimethyl-4,5,6,7-tetrahydro-1H-indole-3-carboxamide.

22. A pharmaceutical composition according to claim 1, comprising a compound which is N-(2-Methylphenyl-4-oxo-6,6-dimethyl-4,5,6,7-tetrahydro-1H-indole-3-carboxamide.

23. A pharmaceutical composition according to claim 1, comprising a compound which is N-(2-Hydroxy-4-methylphenyl)-4-oxo-6,6-dimethyl-4,5,6,7-tetrahydro-1H-indole-3-carboxamide.

24. A pharmaceutical composition according to claim 1, comprising a compound which is N-Phenyl-4-oxo-6-methyl-4,5,6,7-tetrahydro-1H-indole-3-carboxamide.

25. A pharmaceutical composition according to claim 1, comprising a compound which is N-(2-Fluorophenyl)-4-oxo-6-methyl-4,5,6,7-tetrahydro-1H-indole-3-carboxamide.

26. A pharmaceutical composition according to claim 1, comprising a compound which is N-(3-Fluorophenyl)-4-oxo-6-methyl-4,5,6,7-tetrahydro-1H-indole-3-carboxamide.

27. A c pharmaceutical composition according to claim 1 comprising a compound which is N-(4-Fluorophenyl)-4-oxo-6-methyl-4,5,6,7-tetrahydro-1H-indole-3-carboxamide.

28. A pharmaceutical composition according to claim 1, comprising a compound which is N-(3-Methoxyphenyl)-4-oxo-6-methyl-4,5,6,7-tetrahydro-1H-indole-3-carboxamide.

29. A pharmaceutical composition according to claim 1, comprising a compound which is N-(4-Hydroxyphenyl)-4-oxo-6-methyl-4,5,6,7-tetrahydro-1H-indole-3-carboxamide.

30. A pharmaceutical composition according to claim 1, comprising a compound which is N-(2-Fluoro-4-hydroxyphenyl)-4-oxo-6-methyl-4,5,6,7-tetrahydro-1H-indole-3-carboxamide.

31. A pharmaceutical composition according to claim 1, comprising a compound which is N-(2-Hydroxy-4-methoxyphenyl)-4-oxo-6-methyl-4,5,6,7-tetrahydro-1H-indole-3-carboxamide.

32. A pharmaceutical composition according to claim 1, comprising a compound which is N-(4-Methoxyphenyl)-4-oxo-6-methyl-4,5,6,7-tetrahydro-1H-indole-3-carboxamide.

33. A pharmaceutical composition according to claim 1, composition a compound which is N-(2-Fluoro-4-methoxyphenyl)-4-oxo-5-methyl-4,5,6,7-tetrahydro-1H-indole-3-carboxamide.

34. A pharmaceutical composition according to claim 1, comprising a compound which is N-(4-Ethoxyphenyl)-4-oxo-6-methyl-4,5,6,7-tetrahydro-1H-indole-3-carboxamide.

35. A pharmaceutical composition according to claim 1, comprising a compound which is N-(2-Fluoro-4-ethoxyphenyl)-4-oxo-6-methyl-4,5,6,7-tetrahydro-1H-indole-3-carboxamide.

36. A pharmaceutical composition according to claim 1, comprising a compound which is N-(3,4-Dihydroxyphenyl)-4-oxo-6-methyl-4,5,6,7-tetrahydro-1H-indole-3-carboxamide.

37. A pharmaceutical composition according to claim 1, comprising a compound which is N-(2-Hydroxy-4-methylphenyl)-4-oxo-6-methyl-4,5,6,7-tetrahydro-1H-indole-3-carboxamide.

38. A pharmaceutical composition according to claim 1, comprising a compound which is N-(3-Pyridyl)-4-oxo-6,6-dimethyl-4,5,6,7-tetrahydro-1H-indole-3-carboxamide.

39. A pharmaceutical composition according to claim 1, comprising a compound which is N-(4-Methoxy-3-pyridyl)-4-oxo-6,6-dimethyl-4,5,6,7-tetrahydro-1H-indole-3-carboxamide.

40. A pharmaceutical composition according to claim 1, comprising a compound which is N-(3-Pyridyl)-4-oxo-6-methyl-4,5,6,7-tetrahydro-1H-indole-3-carboxamide.

41. A pharmaceutical composition according to claim 1, comprising a compound which is N-(4-Pyridyl)-4-oxo-6-methyl-4,5,6,7-tetrahydro-1H-indole-3-carboxamide.

42. A pharmaceutical composition according to claim 1, comprising a compound which is N-(4-Pyridyl-4oxo-6,6-dimethyl-4,5,6,7-tetrahydro-1H-indole-3-carboxmide.

43. A compound of the formula:

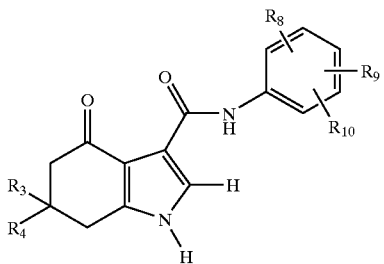

wherein
$R_3$ and $R_4$ are the same or different and represent hydrogen or alkyl, provided that not both $R_3$ and $R_4$ are hydrogen;

$R_6$ is hydrogen, halogen, hydroxyl, alkyl, alkoxy, cycloalkyl alkoxy having 3–7 carbon atoms, amino, mono- or dialkylamino; and $R_6$ is hydrogen, halogen, cyano, hydroxy, alkyl, alkoxy, cyclcalkyl alkoxy having 3–7 carbon atoms, amino, mono- or dialkylamino, $NR_1COR_2$, $COR_2$, or $CO_2R_2$ where $R_1$ and $R_2$ are the same or different and represent hydrogen, alkyl, or cycloalkyl having 3–7 carbon atoms; and $R_{10}$ is hydrogen, halogen, hydroxyl, alkyl, alkoxy, amino, mono- or dialkylamino.

44. A compound according to claim 43 of the formula:

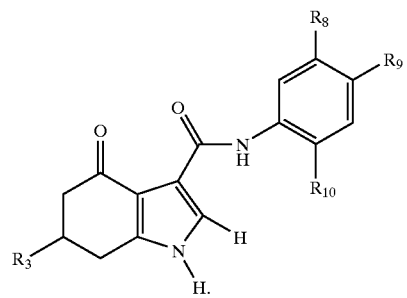

45. A compound according to claim 44 wherein $R_8$, $R_9$, and $R_{10}$ are independently selected from hydrogen, halogen, alkyl, alkoxy, amino, and mono- and dialkylamino.

46. A compound according to claim 43 of the formula:

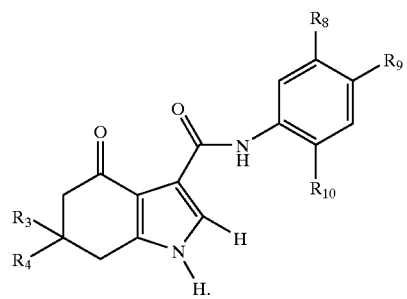

47. A compound according to claim 46, wherein
$R_3$ and $R_4$ are both methyl, and
$R_8$, $R_9$, and $R_{10}$ are independently selected from hydrogen, halogen, hydroxy, alkoxy, and alkyl, provided that not all of $R_8$, $R_9$, and $R_{10}$ are hydrogen.

* * * * *